(12) United States Patent
Desai et al.

(10) Patent No.: US 8,535,345 B2
(45) Date of Patent: Sep. 17, 2013

(54) VASOOCCLUSIVE COIL WITH BIPLEX WINDINGS TO IMPROVE MECHANICAL PROPERTIES

(75) Inventors: Rupesh Desai, San Jose, CA (US); Eric W. Leopold, Redwood City, CA (US)

(73) Assignee: DePuy Synthes Products, LLC, Raynham, MA (US)

( * ) Notice: Subject to any disclaimer, the term of this patent is extended or adjusted under 35 U.S.C. 154(b) by 216 days.

(21) Appl. No.: 10/960,635

(22) Filed: Oct. 7, 2004

(65) Prior Publication Data

US 2006/0079926 A1    Apr. 13, 2006

(51) Int. Cl.
*A61M 29/00* (2006.01)

(52) U.S. Cl.
USPC ........................................................ 606/200

(58) Field of Classification Search
USPC ........ 606/200, 151, 191, 198, 108; 623/1.23, 623/1.11; 128/831, 843
See application file for complete search history.

(56) References Cited

U.S. PATENT DOCUMENTS

| | | | |
|---|---|---|---|
| 1,341,052 A | 5/1920 | Gale | |
| 1,667,730 A | 5/1928 | Green | |
| 2,078,182 A | 4/1937 | MacFarland | |
| 2,549,335 A | 4/1951 | Rahthus | |
| 3,334,629 A | 8/1967 | Cohn | |
| 3,649,224 A | 3/1972 | Anderson et al. | |
| 3,868,956 A | 3/1975 | Alfidi et al. | |
| 4,494,531 A | 1/1985 | Gianturco | |
| 4,512,338 A | 4/1985 | Balko et al. | |
| 4,531,933 A | 7/1985 | Norton et al. | |
| 4,638,803 A | 1/1987 | Rand | |
| 4,655,771 A | 4/1987 | Wallsten | |
| 4,718,907 A | 1/1988 | Karwoski et al. | |
| 4,748,986 A | 6/1988 | Morrison et al. | |
| 4,768,507 A | 9/1988 | Fischell et al. | |
| 4,795,458 A | 1/1989 | Regan | |
| 4,800,882 A | 1/1989 | Gianturco | |
| 4,813,925 A | 3/1989 | Anderson, Jr. et al. | |
| 4,820,298 A | 4/1989 | Leveen et al. | |
| 4,830,003 A | 5/1989 | Wolff et al. | |
| 4,832,055 A | 5/1989 | Palestrant | |

(Continued)

FOREIGN PATENT DOCUMENTS

EP   0183372   6/1986
EP   0 382014 A1   8/1990

(Continued)

OTHER PUBLICATIONS

Sadek K. Hilal, M.D. et al. Journal of Neurological Surgery "Therapeutic Percutaneous Embolization for Extra-Axial Vascular Lesions of the Head, Neck and Spine" Sep. 1975; pp. 275-287.

(Continued)

*Primary Examiner* — Gary Jackson
*Assistant Examiner* — Jonathan Hollm
(74) *Attorney, Agent, or Firm* — Fulwider Patton LLP

(57) ABSTRACT

The vasoocclusive device for use in interventional therapy and vascular surgery adapted to be inserted into a portion of a vasculature, includes a vasoocclusive coil disposed about an inner reinforcement coil wherein said vasoocclusive coil is helically wound and the inner reinforcement coil forms a reverse helical winding opposite the vasoocclusive coil winding, thereby forming a biplex wound coil. The vasoocclusive device biplex winding provides improved mechanical properties to the device. An inner reinforcement stretch resistant member attached within the biplex windings limits coil stretchability.

20 Claims, 4 Drawing Sheets

(56) References Cited

U.S. PATENT DOCUMENTS

| | | |
|---|---|---|
| 4,850,960 A | 7/1989 | Grayzel |
| 4,856,516 A | 8/1989 | Hillstead |
| 4,954,126 A | 9/1990 | Wallsten |
| 4,957,479 A | 9/1990 | Roemer |
| 4,957,501 A | 9/1990 | Lahille et al. |
| 4,990,155 A | 2/1991 | Wilkoff |
| 4,994,069 A | 2/1991 | Ritchart et al. |
| 5,026,377 A | 6/1991 | Burton et al. |
| 5,041,084 A | 8/1991 | DeVries et al. |
| 5,064,435 A | 11/1991 | Porter |
| 5,071,407 A | 12/1991 | Termin et al. |
| 5,104,404 A | 4/1992 | Wolff |
| 5,108,407 A | 4/1992 | Geremia et al. |
| 5,122,136 A | 6/1992 | Guglielmi et al. |
| 5,133,731 A | 7/1992 | Butler et al. |
| 5,133,732 A | 7/1992 | Wiktor |
| 5,141,502 A | 8/1992 | Macaluso, Jr. |
| 5,147,370 A | 9/1992 | McNamara et al. |
| 5,151,105 A | 9/1992 | Kwan-Gett |
| 5,154,705 A * | 10/1992 | Fleischhacker et al. ...... 604/526 |
| 5,160,341 A | 11/1992 | Brenneman et al. |
| 5,176,625 A | 1/1993 | Brisson |
| 5,176,661 A | 1/1993 | Evard et al. |
| 5,183,085 A | 2/1993 | Timmermans |
| 5,186,992 A | 2/1993 | Kite, III |
| 5,203,772 A | 4/1993 | Hammerslag et al. |
| 5,217,484 A | 6/1993 | Marks |
| 5,222,969 A | 6/1993 | Gillis |
| 5,226,911 A | 7/1993 | Chee et al. |
| 5,228,453 A | 7/1993 | Sepetka |
| 5,234,456 A | 8/1993 | Silvestrini |
| 5,250,071 A | 10/1993 | Palermo |
| 5,261,916 A | 11/1993 | Engelson |
| 5,304,194 A | 4/1994 | Chee et al. |
| 5,304,195 A | 4/1994 | Twyford, Jr. et al. |
| 5,312,415 A | 5/1994 | Palermo |
| 5,314,472 A | 5/1994 | Fontaine |
| 5,334,210 A | 8/1994 | Gianturco |
| 5,336,205 A | 8/1994 | Zenzen et al. |
| 5,342,387 A | 8/1994 | Summers |
| 5,345,945 A * | 9/1994 | Hodgson et al. ............... 600/585 |
| 5,350,397 A | 9/1994 | Palermo et al. |
| 5,350,398 A | 9/1994 | Pavcnik et al. |
| 5,354,295 A | 10/1994 | Guglielmi et al. |
| 5,370,683 A | 12/1994 | Fontaine |
| 5,382,259 A | 1/1995 | Phelps et al. |
| 5,423,829 A | 6/1995 | Pham et al. |
| 5,441,516 A | 8/1995 | Wang et al. |
| 5,443,478 A | 8/1995 | Purdy |
| 5,514,176 A | 5/1996 | Bosley, Jr. |
| 5,522,822 A | 6/1996 | Phelps et al. |
| 5,522,836 A | 6/1996 | Palermo |
| 5,527,354 A | 6/1996 | Fontaine et al. |
| 5,536,274 A | 7/1996 | Neuss |
| 5,549,624 A | 8/1996 | Mirigian et al. |
| 5,562,641 A | 10/1996 | Flomenblit et al. |
| 5,562,698 A | 10/1996 | Parker |
| 5,569,245 A | 10/1996 | Guglielmi et al. |
| 5,582,619 A | 12/1996 | Ken |
| 5,607,445 A | 3/1997 | Summers |
| 5,624,449 A | 4/1997 | Pham et al. |
| 5,624,461 A | 4/1997 | Mariant |
| 5,637,113 A | 6/1997 | Tartaglia et al. |
| 5,639,277 A | 6/1997 | Mariant et al. |
| 5,643,254 A | 7/1997 | Scheldrup et al. |
| 5,645,082 A | 7/1997 | Sung et al. |
| 5,645,558 A | 7/1997 | Horton |
| 5,649,949 A | 7/1997 | Wallace et al. |
| 5,667,522 A | 9/1997 | Flomenblit et al. |
| 5,669,931 A | 9/1997 | Kupiecki et al. |
| 5,676,697 A | 10/1997 | McDonald |
| 5,685,322 A | 11/1997 | Sung et al. |
| 5,690,643 A | 11/1997 | Wijay |
| 5,690,666 A | 11/1997 | Berenstein et al. |
| 5,690,671 A | 11/1997 | McGurk et al. |
| 5,700,258 A | 12/1997 | Mirigian et al. |
| 5,707,389 A | 1/1998 | Louw et al. |
| 5,718,711 A | 2/1998 | Berenstein et al. |
| 5,725,546 A | 3/1998 | Samson |
| 5,725,552 A | 3/1998 | Kotula et al. |
| 5,733,329 A | 3/1998 | Wallace et al. |
| 5,749,891 A | 5/1998 | Ken et al. |
| 5,749,894 A | 5/1998 | Engelson et al. |
| 5,766,160 A | 6/1998 | Samson et al. |
| 5,843,118 A | 12/1998 | Sepetka et al. |
| 5,976,162 A * | 11/1999 | Doan et al. .................... 606/151 |
| 6,063,111 A * | 5/2000 | Hieshima et al. ............. 623/1.22 |
| 6,168,570 B1 * | 1/2001 | Ferrera ........................ 600/585 |
| 6,171,326 B1 | 1/2001 | Ferrera et al. |
| 6,193,728 B1 * | 2/2001 | Ken et al. ...................... 606/108 |
| 6,361,558 B1 * | 3/2002 | Hieshima et al. ............. 623/1.16 |
| 6,602,261 B2 | 8/2003 | Greene, Jr. et al. |
| 6,833,003 B2 * | 12/2004 | Jones et al. ................... 623/1.11 |
| 7,166,122 B2 * | 1/2007 | Aganon et al. ................ 606/200 |
| 2002/0002382 A1 * | 1/2002 | Wallace et al. ............... 606/191 |
| 2004/0006354 A1 * | 1/2004 | Schaefer et al. .............. 606/157 |
| 2004/0006363 A1 * | 1/2004 | Schaefer ....................... 606/200 |
| 2004/0034363 A1 * | 2/2004 | Wilson et al. ................. 606/108 |
| 2004/0138695 A1 * | 7/2004 | Li et al. ......................... 606/200 |
| 2005/0171572 A1 * | 8/2005 | Martinez ....................... 606/200 |
| 2006/0036281 A1 * | 2/2006 | Patterson et al. ............. 606/200 |

FOREIGN PATENT DOCUMENTS

| | | |
|---|---|---|
| EP | 0 747 013 A1 | 12/1996 |
| EP | 0747-014 A1 | 12/1996 |
| EP | 0743 047 A3 | 3/1997 |
| EP | 0 765 636 A2 | 4/1997 |
| EP | 0 820 726 A2 | 1/1998 |
| GB | 2066839 | 7/1981 |
| WO | WO 92/14408 | 9/1992 |
| WO | WO 94/09705 | 5/1994 |
| WO | WO 94/10936 | 5/1994 |
| WO | WO 97/31672 | 9/1997 |
| WO | WO 97/48351 | 12/1997 |
| WO | WO 98/09570 | 3/1998 |
| WO | WO 99/29260 | 6/1999 |

OTHER PUBLICATIONS

Stephen L. Kaufman, M.D. et al. Investigative Radiology, May-Jun. 1978 "Transcatheter Embolization With Microfibrillar Collagen in Swine"; pp. 200-204.

Ashok J. Kumar, et al., Journal of Neuroradiology (1982) "Preoperative Embolization of Hypervascular Head and Neck Neoplasms Using Microfibrillar Collagen", pp. 163-168.

Richard E. Latchaw, M.D. et al., Radiology (1979) "Polyvinyl Foam Embolization of Vascular and Neoplastic Lesions of the Head, Neck and Spine" pp. 669-679.

Stewart R. Reuter, M.D. et al. American Journal of Radiology, Sep. 1975 "Selective Arterial Embolization for Control of Massive Upper Gastrointestinal Bleeding" pp. 119-126.

Glenn H. Roberson, et al., American Journal of Radiology, Oct. 1979 "Therapeutic Embolization of Juvenile Angiofibroma" pp. 657-663.

Sidney Wallace, M.D. et al., Cancer, Oct. 1979 "Arterial Occlusion of Pelvic Bone Tumors"; pp. 322-325 & 661-663.

"Mechanical Devices for Arterial Occlusion" by C. Gianturco, M.D., et al., Jul. 1975 pp. 428-435.

"Therapeutic Vascular Occlusion Utilizing Steel Coil Technique: Clinical Applications" by Sidney Wallace, et al., Am J. Roentgenol (1976); pp. 381-387.

Duckwiler et al. "Catheters, Embolic Agents Spark Neurointervention", Diagnostic Imaging, May 1994; pp. 66-70, 102.

"Transcatheter Intravascular Coil Occlusion of Experimental Arteriovenous Fistulas", by James H. Anderson, et al., Am. J. Roentgenol, Nov. 1977, pp. 795-798.

"Mini" Gianturco Stainless Steel Coils for Trancatheter Vascular Occlusion by James H. Anderson, et al. From the Department of Diagnostic Radiology at the University of Texas System Cancer Center, Aug. 1978, pp. 301-303.

"A New Improved Coil for Tapered-Tip Catheter for Arterial Occlusion" by Vincent P. Chuang, M.D., et al. May 1980, pp. 507-509.

"Shape Memory Alloys" by Jeff Perkins, pp. 1095-1096.

Christos A. Athanasoulis, M.D. The New England Journal of Medicine, May 15, 1980 "Therapeutic Applications of Angiography" pp. 1117-1125 (1 of 2).

Christos A. Athanasoulis, M.D. The New England Journal of Medicine, May 22, 1980 "Therapeutic Applications of Angiography" pp. 1174-1179 (2 of 2).

Alex Berenstein, M.D. and Irvin I. Kricheff, M.D. "Catheter and Material Selection for Transarterial Embolization: Technical Considerations" Radiology, Sep. 1979; pp. 631-639.

O.A. Battista, et al. Journal of Applied Polymer Science 1967 "Colloidal Macromolecular Phenomena. Part II. Novel Microcrystals of Polymers" pp. 481-498.

* cited by examiner

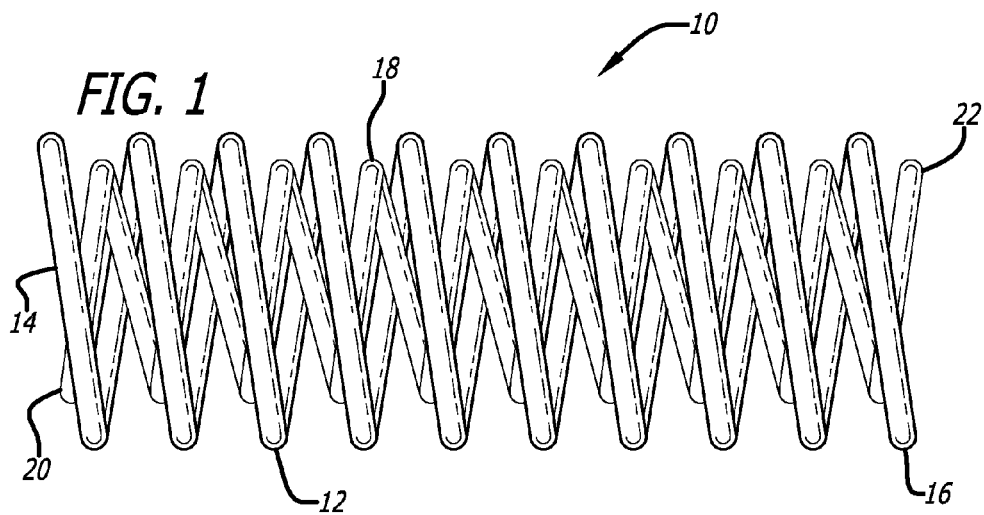
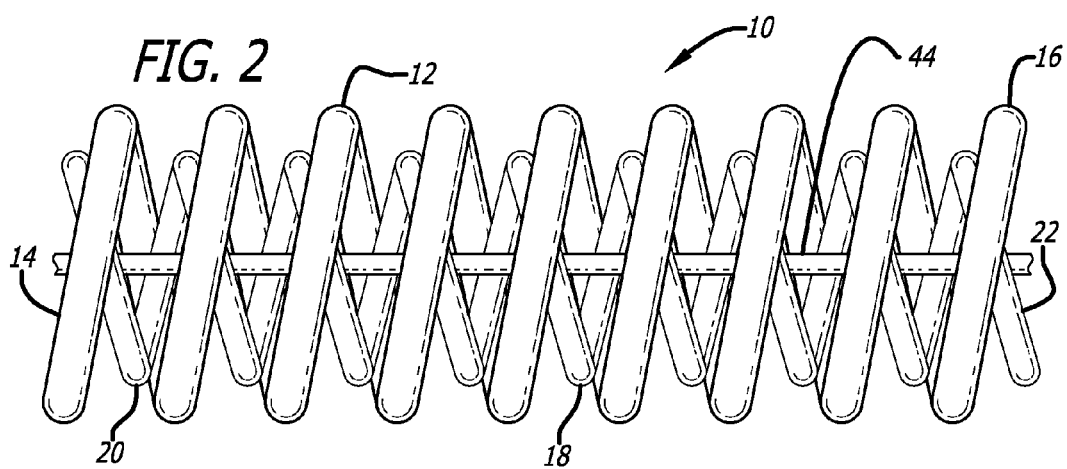
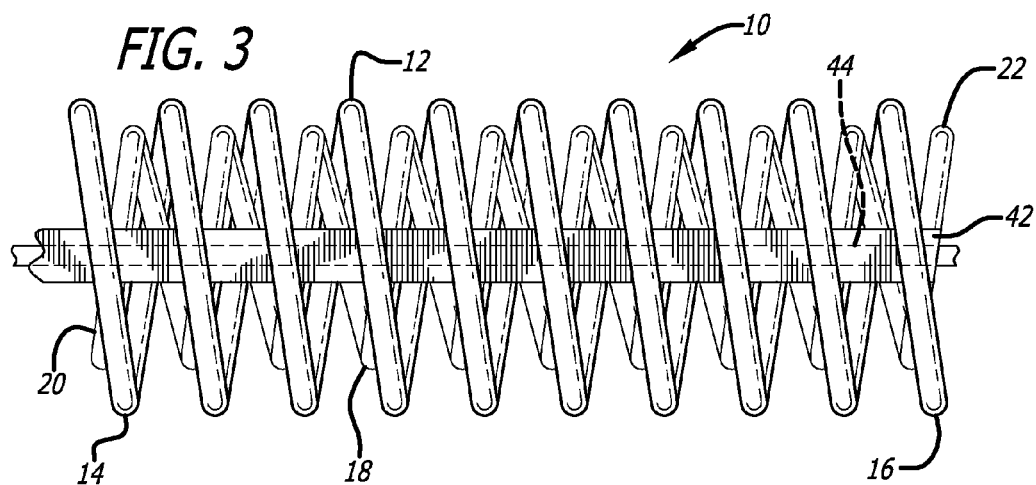

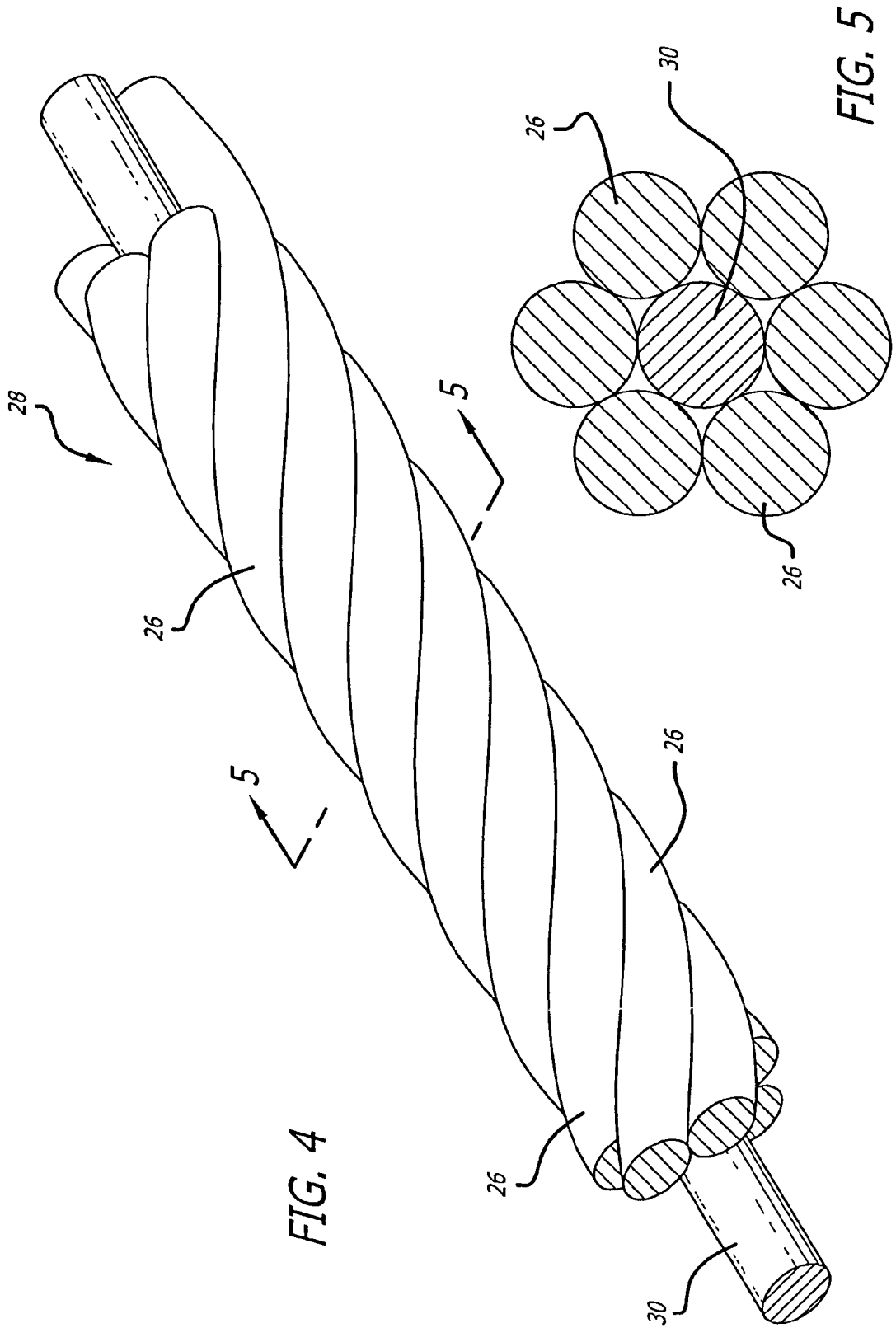

VASOOCCLUSIVE COIL WITH BIPLEX WINDINGS TO IMPROVE MECHANICAL PROPERTIES

BACKGROUND OF THE INVENTION

1. Field of the Invention

This invention relates generally to devices for intravascular interventional therapeutic treatment or vascular surgery for treatment of defects in the vasculature, and more particularly concerns an improved vasoocclusive coil, such as for treatment of aneurysms.

2. Description of Related Art

The art and science of interventional therapy and surgery has continually progressed towards treatment of internal defects and diseases by use of ever smaller incisions or access through the vasculature or body openings in order to reduce the trauma to tissue surrounding the treatment site. One important aspect of such treatments involves the use of catheters to place therapeutic devices at a treatment site by access through the vasculature. Examples of such procedures include transluminal angioplasty, placement of stents to reinforce the walls of a blood vessel or the like and the use of vasoocclusion devices to treat defects in the vasculature. There is a constant drive by those practicing in the art to develop new and more capable systems for such applications. When coupled with developments in biological treatment capabilities, there is an expanding need for technologies that enhance the performance of interventional therapeutic devices and systems.

One specific field of interventional therapy that has been able to advantageously use recent developments in technology is the treatment of neurovascular defects. More specifically, as smaller and more capable structures and materials have been developed, vascular defects in the human brain which were previously untreatable or represented unacceptable risks via conventional surgery have become amenable to treatment. One type of non-surgical therapy that has become advantageous for the treatment of defects in the neurovasculature has been the placement by way of a catheter of vasoocclusive devices in a damaged portion of a vein or artery.

Vasoocclusive devices are therapeutic devices that are placed within the vasculature of the human body, typically via a catheter, either to block the flow of blood through a vessel making up that portion of the vasculature through the formation of an embolus or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. One anatomically shaped vasoocclusive device that forms itself into a shape of an anatomical cavity such as an aneurysm and is made of a pre-formed strand of flexible material that can be a nickel-titanium alloy is known from U.S. Pat. No. 5,645, 558, which is specifically incorporated by reference herein. That vasoocclusive device comprises one or more vasoocclusive members wound to form a generally spherical or ovoid shape in a relaxed state. The vasoocclusive members can be a helically wound coil or a co-woven braid formed of a biocompatible material, and the device is sized and shaped to fit within a vascular cavity or vesicle, such as for treatment of an aneurysm or fistula. The vasoocclusive member can be first helically wound or braided in a generally linear fashion, and is then wound around an appropriately shaped mandrel or form, and heat treated to retain the shape after removal from the heating form. Radiopacity can be provided in the vasoocclusive members by weaving in synthetic or natural fibers filled with powdered radiopaque material, such as powdered tantalum, powdered tungsten, powdered bismuth oxide or powdered barium sulfate.

The delivery of such vasoocclusive devices can be accomplished by a variety of means, including via a catheter in which the device is pushed through the catheter by a pusher to deploy the device. The vasoocclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

For treatment of areas of the small diameter vasculature such as a small artery or vein in the brain, for example, and for treatment of aneurysms and the like, micro-coils formed of very small diameter wire are used in order to restrict, reinforce, or to occlude such small diameter areas of the vasculature. A variety of materials have been suggested for use in such micro-coils, including nickel-titanium alloys, copper, stainless steel, platinum, tungsten, various plastics or the like, each of which offers certain benefits in various applications. Nickel-titanium alloys are particularly advantageous for the fabrication of such micro-coils, in that they can have superelastic or shape memory properties, and thus can be manufactured to easily fit into a linear portion of a catheter, but attain their originally formed, more complex shape when deployed.

One conventional vasoocclusive coil is known, for example, that has a three dimensional in-filling coil configuration, formed by winding a wire into a helix, and then winding the helix into a secondary form which forms a generally spherical shape, by winding the primary coil about poles placed on winding mandrel. The secondary wound coil is then annealed on the winding mandrel, and the coil is then removed from the winding mandrel and loaded into a carrier for introduction into a delivery catheter. Another similar type of vasoocclusive device is known that can be formed from one or more strands, and can be wound to form a generally spherical or ovoid shape when released and relaxed at the site to be treated. Another implantable vasoocclusive device having multiple secondary layers of primary windings has a final shape that is a generally spherical coil formed of linear or helical primary coils that are wound into a secondary form having three layers. The inner winding is wound and then the second layer formed by winding in the opposite direction of the first layer. The final configuration is a chunky or stepped shape approximately a sphere, ovoid, or egg. Yet another conventional implant for vessel occlusion is made from helical elements of metal or synthetic material by twisting or coiling the elements and forming them into a secondary shape such as a rosette or double rosette for implantation using a catheter, and another vasoocclusive device is known that has a final conical shape. However, due to the tendency of such three dimensional shaped coils to transform into their expanded, final forms when introduced into a catheter in the body, they are inherently more difficult than a helical coil or a straight wire or micro-cable to push through such a catheter for delivery to a site in the vasculature to be treated, due to friction between the coil and the catheter through which it is delivered to the site to be treated, which can even result in misalignment of the coil within the catheter during delivery.

Vasoocclusive coils made of platinum, gold, and other ductile materials will easily deform from their coil shape under tension, causing a potentially dangerous situation when the coil is partially in an aneurysm and partially stretched in the delivery catheter. If it is determined that the coil is improperly placed, or is too large, the coil will need to be moved or replaced. However, at this stage of the procedure, the coil can no longer be pushed, and must be slowly retracted out of the catheter as a wire. If during this procedure the coil breaks, an additional procedure must be performed to remove the coil extending out of the aneurysm. It would be desirable to reinforce such vasoocclusive coils to provide stretch resistance to the coils to reduce the risk of the coils breaking, particularly during withdrawal of a coil for relocation or replacement, in order to provide a safety factor during retraction of soft or otherwise easily stretchable coils. It would also be desirable to minimize the increase of stiffness caused by reinforcement of the coils after the coils are released in deployment of the coils in an aneurysm so that the coils can freely transform to a desired secondary shape and conform to the dimensions of the location being treated. It would also be desirable to provide a vasoocclusive coil with additional therapeutic properties to enhance the effectiveness of treatment. The present invention meets these and other needs.

SUMMARY OF THE INVENTION

Briefly, and in general terms, the present invention provides for a vasoocclusive device having biplex wound coils which comprises a helically wound vasoocclusive coil disposed about an inner reinforcement coil having a reverse helical winding, in which the device is deployed through a catheter to an area in the vasculature to be treated. The vasoocclusive coil with biplex windings improve the mechanical properties of the coil.

The invention accordingly provides for a vasoocclusive device for use in interventional therapy and vascular surgery that is adapted to be inserted into a portion of a vasculature. The vasoocclusive device comprises a vasoocclusive coil having a proximal and a distal end and defining a lumen between the proximal and distal ends, an inner reinforcement coil extending through the lumen of the vasoocclusive coil, and the inner reinforcement coil forms a helical winding opposite the winding of the vasoocclusive coil. Advantageously, the biplex winding improves the vasoocclusive coil mechanical properties. The dual helically wound coils of the biplex winding are configured to enhance the vasoocclusive coil stiffness without using large diameter wires in the primary. The biplex windings provide a reinforced coil structure that reduces coil interlocking and virtually eliminates kinking between coils. In a presently preferred aspect, the inner coil is wound in a helical form opposite to the winding of the outer coil to further enhance the characteristics of the biplex coil, although in another aspect the inner coil may be wound in the same direction as the outer coil.

In a presently preferred embodiment of the invention, the vasoocclusive coil biplex windings preferably extend along a longitudinal axis, the inner reinforcement coil winding being wound opposite the outer vasoocclusive coil, thereby curving about the longitudinal axis to form a hollow cylindrical pattern of helical and reversed helical coil configurations. In a preferred aspect, the biplex wound coils having proximal and distal ends are fixedly attached at the proximal ends of the vasoocclusive coil and inner reinforcement coil. The first helical coil and the second opposite wound coil may be attached by conventional methods including adhesives or heat bonding. In another presently preferred aspect, the first coil and second coil may not be fixedly attached. The second coil may be manufactured to be securely positioned within the first coil without fixation means, thereby providing a vasoocclusive coil having greater flexibility.

In another preferred embodiment, the vasoocclusive coil is formed from at least one multi-stranded micro-cable formed of a plurality of flexible strands of a resilient material. The inner reinforcement coil is also formed from at least one multi-stranded cable. By using the stranded or micro-cable construction of the invention, the vasoocclusive device becomes virtually kink resistant. In another preferred aspect, the multi-stranded biplex cable incorporates a radiopaque material in either the vasoocclusive cable, the inner reinforcement cable or preferably both coils to provide enhanced radiopacity.

The present invention also provides for a vasoocclusive device having vasoocclusive coil biplex windings and an inner reinforcement stretch resistant member extending through the vasoocclusive coil lumen to provide increased stretch resistance to the vasoocclusive coil. The reinforcement stretch resistant member also allows the coil to be pushed even when such a coil is partially deployed, to improve safety during retraction of the coil. The stretch resistant member may be formed as a ribbon, wire, braid, a coil such as a primary wind, or stranded material, and may be formed of a therapeutic or bioactive material.

In a further presently preferred embodiment, an inner strand of bioactive material may be inserted through the center of the inner coil to further enhance the mechanical characteristics of the coil assembly, improve stretch resistance and provide other benefits to the operation of the coil.

These and other aspects and advantages of the invention will become apparent from the following detailed description and the accompanying drawings, which illustrate by way of example the features of the invention.

BRIEF DESCRIPTION OF THE DRAWINGS

FIG. 1 is a side elevational view illustrating a preferred embodiment of the vasoocclusive coil biplex windings.

FIG. 2 is the vasoocclusive device of FIG. 1, depicting a vasoocclusive coil having increased coil density.

FIG. 3 is the vasoocclusive device of FIG. 1, further depicting a vasoocclusive device having an inner reinforcement stretch resistant member extending through the vasoocclusive coil biplex windings.

FIG. 4 is a perspective of a multi-stranded micro-cable constructed according to the invention.

FIG. 5 is a cross-section at 5-5 of FIG. 4.

DETAILED DESCRIPTION OF THE PREFERRED EMBODIMENTS

Figure 6:
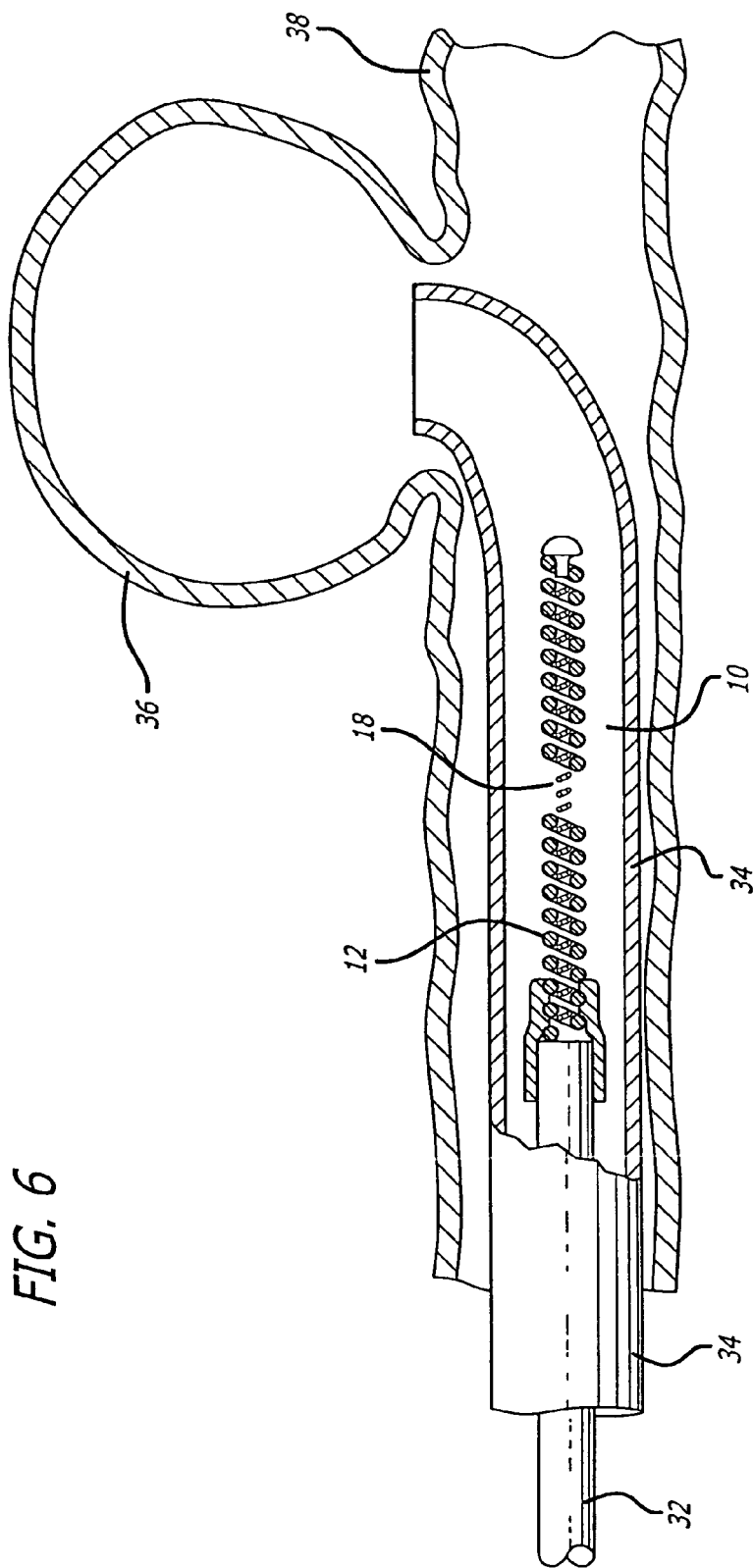
FIG. 6 is a cross sectional view of a vascular member with an aneurysm illustrating the approach of vasoocclusive coil biplex windings towards the aneurysm.

While nickel-titanium alloys are useful in forming superelastic or shape memory interventional devices, micro-coils formed of very small diameter wires of nickel-titanium alloy material for treatment of areas of the small diameter vasculature such as an artery or vein in the brain, for treatment of aneurysms and the like, for example, can have relatively low yield strengths and are somewhat subject to kinking, even if made of super-elastic alloy. This can create problems during placement and if the coil is to be withdrawn after being emplaced by the doctor, as for instance, if the device is too small to effectively fill the cavity to be treated. Furthermore, even solid wires of a size suitable for use in interventional devices are not very radiopaque.

As is illustrated in the drawings, which are provided for the purposes of illustration and not by way of limitation, the invention is embodied in a micro-coil formed of at least one flexible strand of a resilient material having a helically wound coil and a second reverse helical shaped coil, or opposite wound coil, configured within the micro-coil. The vasoocclusive coil is formed of at least one strand of a flexible material formed to have a first helically wound coil, having a proximal and a distal end, and defining a lumen between the proximal and distal ends. A second helically wound coil extends through the lumen of the first coil, forming a vasoocclusive coil having biplex windings for insertion through a catheter into a desired portion of the vascular to be treated, such as an aneurysm, or other anatomical malformation of the vasculature to be treated. Advantageously, the biplex winding improves the vasoocclusive coil mechanical properties. The dual helically wound coils of the biplex winding are configured to enhance the vasoocclusive coil stiffness without using large diameter wires in the primary. The biplex windings provide a reinforced coil structure that reduces coil interlocking and virtually eliminates kinking between coils.

Figure 7:
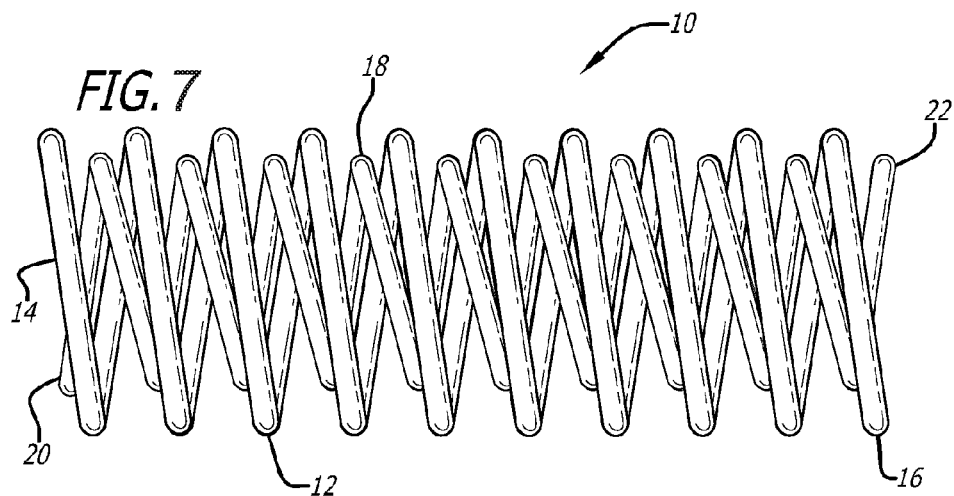
FIG. 7 is a side elevational view illustrating an alternate preferred embodiment of the vasoocclusive coil biplex windings with the inner reinforcement coil forming a helical winding wound in the same direction as the vasoocclusive coil winding.
Figure 8:
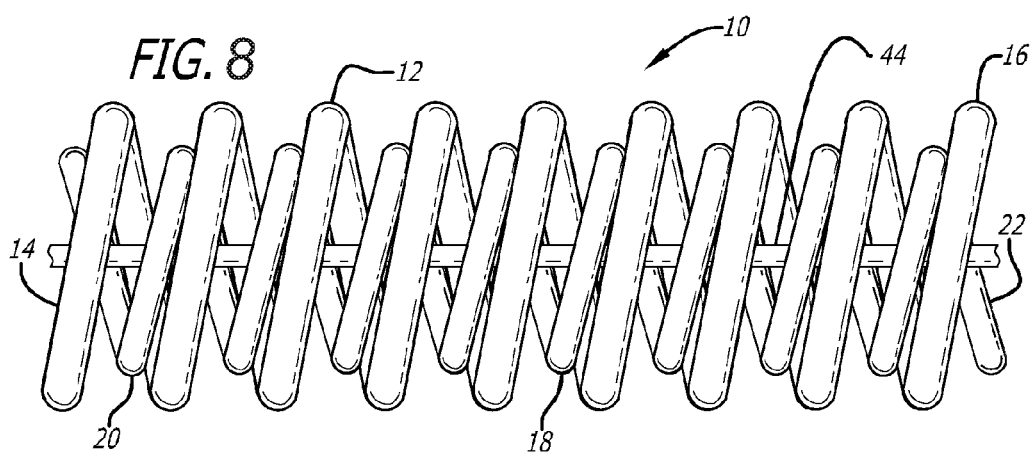
FIG. 8 is the vasoocclusive device of FIG. 7, depicting a vasoocclusive coil having increased coil density.
Figure 9:
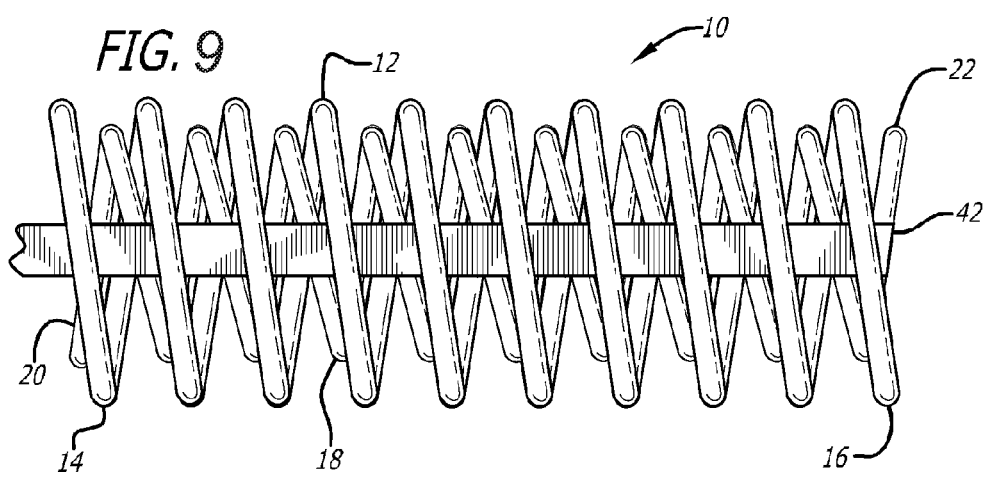
FIG. 9 is the vasoocclusive device of FIG. 7, further depicting a vasoocclusive device having an inner reinforcement stretch resistant member extending through the vasoocclusive coil biplex windings.

As shown in FIGS. 1-3, in a presently preferred embodiment, the vasoocclusive coil biplex windings 10 preferably extend along a longitudinal axis, the inner reinforcement coil 18 being wound opposite the outer vasoocclusive coil 12, thereby curving about the longitudinal axis to form a hollow cylindrical pattern of helical and reversed helical coil configurations. In a presently preferred aspect, the biplex wound coils 10 having proximal and distal ends are fixedly attached at the proximal ends of the vasoocclusive coil 14 and inner reinforcement coil 20. The first helical coil 12 and the second opposite wound coil 18 may be attached by conventional methods including adhesives, solder, or heat bonding. Alternatively, those skilled in the art can appreciate that the vasoocclusive coil disposed about an oppositely wound coil may be fixedly attached at the coil distal ends 16 and 22 or at an intermediate region on the coils. Alternatively, the inner reinforcement coil 18 may be wound in the same direction as the outer coil 12, as is illustrated in FIGS. 7-9. It is conceived that the coils of this invention may be fixedly attached at more than one region of the coil. In another presently preferred aspect, the first coil 12 and second coil 18 may not be fixedly attached. The second coil 18 may be manufactured to be securely positioned within the first coil without fixation means, thereby providing a vasoocclusive coil having greater flexibility.

The vasoocclusive coil biplex windings may be formed from a variety of materials including, but not limited to, one or more strands of a metal or metal alloy such as stainless steel or a nickel-titanium alloy, which may include a radiopacity strand forming both the first coil and the second coil. The coils may include a radiopaque strand made of platinum, tungsten or gold, in order to serve as a marker. Other materials, such as shape memory alloys, may also be used to provide for the dual purposes of ease of insertion into a micro-catheter and formation upon deployment into the desired biplex helical configuration. Preferably, the inner reinforcement coil and outer vasoocclusive coil of the present invention are formed of a platinum-tungsten alloy to provide the desired vasoocclusive coil and inner reinforcement coil softness while improving other coil characteristics. In another aspect, the vasoocclusive coil and the inner reinforcement coil are formed from different materials. For example, the inner reinforcement coil may be formed of a bioactive material, such as a swelling material such as a hydrogel, polyglycolic acid or polyglycolide (PGA), or poly(D,L-lactic acid-co-glycolic acid) (PGLA), although other similar bioactive materials may also be suitable. As used herein, the term "hydrogel" refers to a broad class of polymeric materials that have an affinity for water and typically swell in water, but which do not necessarily dissolve in water.

Generally speaking, when the vasoocclusive device 10 is formed of a metal such as platinum or a super-elastic alloy such as NITINOL, the diameter of the wire used in the production of the coil will be in the range of 0.0005 and 0.006 inches. The wire of such diameter is typically then wound into a coil having a primary diameter of between 0.005 and 0.018 inches. The preferable diameter is 0.010 to 0.018 inches. The wire should be of sufficient diameter to provide a hoop strength to the resulting device sufficient to hold the device 10 in place within the chosen vasculature or body cavity without distending the wall of the cavity and without moving from the cavity as a result of the repetitive fluid pulsing found in the vascular system. The overall diameter of the device in the operable configuration is generally between 3 and 40 millimeters. Most aneurysms within the cranial vasculature can be treated by one or more devices having those diameters.

In reference to FIGS. 1 and 2, the characteristics of the vasoocclusive device can be further improved by altering the geometry of the vasoocclusive coil 12. FIG. 2 depicts vasoocclusive coil biplex windings 10 wherein the outer vasoocclusive coil 12 has an increased coil diameter to provide greater contact surface area to anchor the device to the area to be treated. Varying the vasoocclusive coil diameter also impacts the degree of flexibility and stretchability for the biplex windings. In addition, by varying the coil pitch of the helix the conformity of the device to the vascular walls can be enhanced, and variation of the biplex pitch can provide a desired exposure of bioactive material in the coil, as is explained further hereinbelow. The characteristics of the device such as loop strength and the resilience of the device are controlled by the radii of the transitions from the outer vasoocclusive coil 12 to the inner reinforcement coil 18 and the distance between the parallel loop windings. By use of the invention, a variety of densities may be provided in the coil to coil distance, thus assisting in the treatment of various malformations.

In another presently preferred embodiment, the invention is embodied in a multi-stranded micro-cable formed of a plurality of flexible strands of a resilient material with the cable including at least one radiopaque strand 30. In a presently preferred embodiment of the invention illustrated in FIG. 1, the multi-stranded micro-cable 28 is approximately 0.0015 to 0.009 inches in diameter, and comprises a plurality of flexible strands 26 of nickel-titanium alloy, with at least one centrally, axially disposed radiopaque wire 30 which is approximately from 0.0005 to 0.003 inches in diameter. While the above stated diameters represent those presently known to be compatible with the invention, larger or smaller diameters may be useful for particular applications. The central radiopaque wire 30 can be formed of platinum or gold, for example, or other similar suitable radiopaque metals, in order to provide a radiopaque marker for the deployed configuration of a device made of the cable during vascular surgery.

There are numerous benefits to the novel biplex winding 10 construction of the invention for use in interventional devices and the like. By using the stranded 26 or micro-cable 28 construction of the invention, a biplex wound device made from the micro-cable becomes virtually kink resistant compared to the single strand wires now commonly used in micro-coils. As shown in FIG. 4, the multi-strand biplex cable construction of the invention allows the micro-wires of the cable to slip across each other and reinforce each other rather than break or take a set. Also, by incorporating a stranded radiopaque material such as platinum, tungsten or gold into the cable construction, the vasoocclusive device is radiopaque in sizes much smaller than with other constructions. The micro-cable biplex construction of the invention can be used to produce soft, kink resistant, radiopaque stents, guidewires, guidewire distal tips, and micro-coils.

FIG. 5 is a cross-section of the micro-cable of FIG. 4 at 5-5 illustrating one presently preferred arrangement of the strands within the cable. In this embodiment, the exterior strands 26 are formed of a resilient material chosen to provide the characteristics desired for a specific application in interventional therapies. In a presently preferred embodiment, this material is a platinum tungsten alloy which provides desired coil stiffness, softness, and stretchability. Another preferred material is a nickel titanium super-elastic alloy which is heat treated such that the alloy is highly flexible at a temperature appropriate for introduction into the body via a catheter. By choosing such a material for micro-coils and the like, the devices formed from the micro-cable can be relatively easily placed into the appropriate body cavity and after placement, the device will take on a shape designed to optimize the therapeutic purposes desired for the device. As illustrated in FIG. 5, such a cable can have a central core 30 of a radiopaque material such as gold or platinum, thus dramatically enhancing the radiopacity of the cable. Even a solid super-elastic wire of the same diameter as the cable would have substantially less radiopacity than the biplex cable of the invention with the central gold or platinum wire and the construction of the invention provides numerous other highly desirable characteristics. Among these characteristics is the relative flexibility and resistance to kinking of the cable compared to an equivalent single wire and substantially greater accommodation of the cable to bending, etc., with resultant lessening of trauma to the surrounding tissue and ease of placement in a small body cavity.

One advantageous application of the invention is to vasoocclusive devices formed of the micro-cable for insertion into aneurysms and other vascular defects for the purpose of occluding flow to the aneurysm. FIG. 6 illustrates a helically wound biplex coil 10 of micro-cable 28 which is formed to fit within a micro-catheter 34 for insertion into an area upon which a therapeutic procedure is to be performed. While a helical coil is illustrated, it will be appreciated that numerous other secondary shapes can be formed from the cable of the invention, as will be described further below. More specifically, a three dimensional, essentially spherical, device (not shown) can be formed of the cable, at a temperature sufficient to heat treat the material and thereby create a memory of the desired shape. The device is then inserted into a catheter 34 from which it may be deployed into an aneurysm or the like. The teachings of U.S. Pat. No. 5,645,558 describe the construction of such a device out of flexible wire and are incorporated by referenced herein.

FIG. 6 is an illustration of a catheter 34 using a coil 10 as a vasoocclusive device made of the present invention and used for insertion into an aneurysm 36 projecting laterally from a blood vessel 38. The coil 10 is contained within the outer housing of a micro-catheter 34 that is used to house the coil prior to deployment. The end of the catheter housing 34 is introduced into the opening of the aneurysm 36 by use of a guide wire (not shown). Thereafter, the vasoocclusive coil 10, and a pusher member 32 are introduced into the catheter to provide for insertion of the vasooclusive device into the aneurysm.

Those skilled in the art will recognize that it is sometimes the case that the vasooclusive device must be withdrawn after it is frilly or partly inserted into the aneurysm. In such a case, there is a danger that the coil will be stretched beyond its elastic range or kink, or otherwise deform and make withdrawal difficult. Those skilled in the art will also recognize that it is sometimes advantageous to form vasooclusive devices of secondary shapes which are based upon a basic configuration of a coil or the like. The present invention includes such applications within the scope of the invention. However, when vasooclusive devices made of even super-elastic material are used, it is sometimes the case that the devices will be stretched or kinked when withdrawal is attempted. The biplex wound cable of the present invention substantially reduces the probability that kinking or stretching beyond yield will occur in a given instance, while at the same time providing radiopacity not available with other constructions. Thus, the present invention represents an important forward step in the technology of interventional therapy.

Those skilled in the art will recognize that a number of shaped devices may be introduced into an area to be treated depending upon its geometry and the number of devices to be inserted. An essentially spherical device which has been deployed into such an aneurysm will commonly be found that the device would then be supplemented by a further coiled device inserted within the space inside the spherical device to completely occlude flow from the artery to the aneurysm.

While one presently preferred implementation of the micro-cable of the invention has been illustrated, those skilled in the art will appreciate that other variations of the invention may have advantages for certain purposes. Referring to FIGS. 1 and 2, an example of one such construction in which radiopacity is more desirable than in other forms and for that reason a number of radiopaque strands 30 may be formed into the cable both along the vasooclusive coil 12 and the inner reinforcement coil 18 of the biplex windings. It will also be appreciated that a larger or smaller number of strands may be incorporated into a given cable and the biplex cables may be formed of multiple cables in order to provide desired bending and strength characteristics. It will also be appreciated by those skilled in the art that the invention is adaptable to the use of a variety of materials which by themselves would not have been easily adaptable to micro devices for interventional therapies. For instance, materials such as copper are useful for intrauterine devices and the like, but copper wire, even when heavily alloyed, has certain limitations for use in such devices. By use of the present invention, composite cables incorporating one or more strands of a desired material can be configured with other strands providing strength, flexibility, shape memory, super-elasticity, radiopacity or the like for previously unavailable characteristics in micro devices.

The invention is also adaptable to numerous other purposes, a further preferred embodiment in which radiopaque strands and resilient strands form a portion of the cable 10 and a therapeutic agent is contained in one of the strands. Such a therapeutic agent can include human growth hormone, hydrogels, or a variety of other agents which will serve to provide desired therapeutic capabilities when placed within a specific area of the body being treated by use of the micro-catheter. Depending upon the application of the therapeutic agent, its method of action and the delay, if any, in the time after placement in which the therapeutic action is desired, the agent strand may be placed in any of a variety of positions with the cable, from core wire outward. Also, it may be desirable to coat one or more strands with a therapeutic material for certain purposes. At least one of the strands in the core or exterior strands can comprise a therapeutic agent, such as a copper or copper alloy wire or any of a variety of therapeutically active metals, alloys or components, a fiber such as Dacron (polyester), polyglycolic acid, polylactic acid, fluoropolymers, nylon, polyaramid fiber (e.g. Kevlar®), or silk chosen for thrombogenicity. Since the micro-cable consists of stranded parts, one or more strands may be longer than others, or even intermittently terminated, to thereby extend beyond the diameter of the remaining strands and thereby increase the therapeutic effect of that strand. Alternatively, at least one of the strands can be coated with or impregnated with a therapeutic material, which can include, but is not limited to, any one or combination of human growth hormone, genetic material, antigens, hydrogels, collagen, bio-absorbable polymers such as lactic acids/glycolic acids, caprolactam or microcellular foam.

As there are many advantages to having an exposed core coil, it is also contemplated within the scope of the invention that one or more of the strands of the micro-cable is longer than the others, and perhaps intermittently terminated, to thereby produce a micro-cable in which the therapeutic strands extend to a greater diameter than the other strands to thus increase the therapeutic effect of the therapeutic stand. Such a construction is particularly advantageous if increased thrombogenicity is desired, while maintaining structural continuity and radiopacity for the micro-cable.

As illustrated in FIG. 3 and FIG. 9, another presently preferred embodiment provides a vasoocclusive device having biplex windings 10 and being further reinforced by an inner stretch resistant member 42 that extends through the lumen of the vasoocclusive coil, and therein being fixedly attached at one end of at or near a distal end of the vasoocclusive biplex coil 10. Attachment of the inner stretch reinforcement member 42 may also allow the coil to be pushed even when such a coil is partially deployed, to improve safety during retraction of the coil. In another preferred aspect, the vasoocclusive coil 12 may be coated with one or more therapeutic agents, which may include a hydrogel. Alternatively, the inner stretch resistant member 42 may be formed of a therapeutic non-metallic material to provide further therapeutic properties to the vasoocclusive biplex coils.

The inner stretch resistant member 42 may extend non-helically through the lumen of the vasoocclusive coil 18 and externally of the inner reinforcement coil 18. The vasoocclusive device may further include an inner strand of bioactive material disposed in the center of the inner reinforcement coil 18.

As is shown in FIG. 2 and FIG. 8, in a further presently preferred embodiment, an inner strand 44 of bioactive material may be inserted through the center of the inner coil to further enhance the mechanical characteristics of the coil assembly, improve stretch resistance and provide other benefits to the operation of the coil. The inner reinforcement stretch resistant member 42 and the inner strand of bioactive material 44 may be formed from a therapeutic and/or bioactive non-metallic fiber material, such as silk, collagen, elastin or other connecting proteins, polyglycolic acid or polyglycolide (PGA), polylactic acid or poly(D,L-lactide) (PLA), poly(D,L-lactic acid-co-glycolic acid) (PGLA) or poly(D, L-lactide-co-glycolide) (PLA/PGA), poly(L-lactide) (PLLA), poly(L-lactide-co-D,L-lactide) (PLLA/PLA), poly (L-lactide-co-glycolide) (PLLA/PGA), poly(glycolide-co-trimethylene carbonate) (PGA/PTMC), polyethylene oxide (PEO), polydioxanone (PDS), polycaprolactone (PCL), hylauric acid, polyhydroxylbutyrate (PHBT), poly(phosphazene), poly(D,L-lactide-co-caprolactone) (PLA/PCL), poly(glycolide-co-caprolactone) (PGA/PCL), polyvinyl alcohol (PVA), polyanhydrides (PAN), poly(ortho esters), poly(phosphate ester), poly(amino acid), poly(hydroxy butyrate), copolymers of these materials as well as composites and combinations thereof, plastic or other polymers such as an ethylene-octene copolymer, polypropylene, polyethylene, polyacrylate, polyacrylamide, poly(hydroxyethyl methacrylate), polyurethane, polysiloxane and their copolymers. The therapeutic and/or bioactive non-metallic fiber material may be bioabsorbable, such as PGA, for example, or non-absorbable, such as polypropylene, for example. The therapeutic and/or bioactive non-metallic fiber material may also be used for absorbing and releasing one or more therapeutic agents.

The inner reinforcement stretch resistant member 42 can be used to enhance radiopacity, aid in secondary shape configurations, and can be configured to aid desired stiffness of the coil, and can allow a softer coil to be used without stretching of the coil. The inner reinforcement stretch resistant member 42 may be formed from a metal or metal alloy, which may be a radiopaque metal, such as platinum, for example, and may be coated with or formed of a therapeutic or bioactive material as described above. The inner reinforcement stretch resistant member may be formed as a ribbon, wire, braid, a coil, such as a primary wind, or a stranded material. It is conceivable that the inner stretch resistant member, the vasoocclusive coil and the inner reinforcement coil are all formed from a platinum tungsten alloy.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A vasoocclusive device for use in interventional therapy and vascular surgery adapted to be inserted into a portion of a vasculature, comprising:
   a pusher member;
   a vasoocclusive coil having a proximal end and a distal end, said vasoocclusive coil being helically wound forming a lumen between said proximal and distal ends, said vasoocclusive coil being configured to be releasably attached to said pusher member for deployment in the portion of the vasculature;
   an inner reinforcement coil having a center, a proximal end and a distal end, said vasoocclusive coil being disposed about said inner reinforcement coil, said inner reinforcement coil being securely positioned within said vasoocclusive coil without being fixedly attached to said vasoocclusive coil;
   an inner strand of bioactive material disposed in the center of said inner reinforcement coil;
   an inner reinforcement stretch resistant member extending non-helically through the lumen of said vasoocclusive coil and externally of said inner reinforcement coil, said vasoocclusive coil and said inner reinforcement coil together forming a biplex coil, and said inner reinforcement stretch resistant member consisting of a non-metallic fiber material having an end fixedly attached at or near the distal end of said vasoocclusive coil and said inner reinforcement coil of said biplex coil, said inner reinforcement stretch resistant member being configured to allow said vasoocclusive coil to be pushed after said vasoocclusive coil is partially deployed; and said inner reinforcement coil forming a helical winding wound in the same direction as said vasoocclusive coil winding.

2. The vasoocclusive device of claim 1, wherein said vasoocclusive coil is formed from at least one multi-stranded cable.

3. The vasoocclusive device of claim 1, wherein said inner reinforcement coil is formed from at least one multi-stranded cable.

4. The vasoocclusive device of claim 3, wherein said at least one multi-stranded cable includes a plurality of strands, and at least one of the plurality of strands is impregnated with said therapeutic agent.

5. The vasoocclusive device of claim 3, wherein said at least one multi-stranded cable includes a plurality of strands, and at least one of the plurality of strands is coated with said therapeutic agent.

6. The vasoocclusive device of claim 1, wherein said vasoocclusive coil is formed from a metal.

7. The vasoocclusive device of claim 1, wherein said inner reinforcement coil is formed from a metal.

8. The vasoocclusive device of claim 1, wherein said vasoocclusive device is formed from a material selected from the group consisting of platinum and tungsten alloy.

9. The vasoocclusive device of claim 1, wherein said inner reinforcement coil is formed from a material selected from the group consisting of platinum and tungsten alloy.

10. The vasoocclusive device of claim 1, wherein said inner reinforcement coil is radiopaque.

11. The vasoocclusive device of claim 1, wherein said inner reinforcement coil is formed of a bioactive material.

12. The vasoocclusive device of claim 1, wherein said bioactive material comprises a swelling material.

13. The vasoocclusive device of claim 1, wherein said bioactive material is selected from the group consisting of PGA and PGLA.

14. The vasoocclusive device of claim 1, wherein said inner reinforcement coil and said inner strand of bioactive material each comprise a therapeutic agent selected from the group consisting of human growth hormone; genetic material; antigens; hydrogels; a metal wire selected from the group consisting of copper and copper alloys; and a fiber selected from the group consisting of polyester, polyglycolic acid, polylactic acid, fluoropolymers, nylons, polyaramid fiber and silk chosen for thrombogenicity.

15. The vasoocclusive device of claim 1, wherein said inner reinforcement stretch resistant member is formed of a ribbon.

16. The vasoocclusive device of claim 1, wherein said inner reinforcement stretch resistant member is formed of a wire.

17. The vasoocclusive device of claim 1, wherein said inner reinforcement stretch resistant member is formed of a coil.

18. The vasoocclusive device of claim 1, wherein said inner reinforcement stretch resistant member is formed of a bioactive material.

19. A vasoocclusive device for use in interventional therapy and vascular surgery adapted to be inserted into a portion of a vasculature, comprising:

a pusher member;

a vasoocclusive coil releasably attached to said pusher member for deployment in the portion of the vasculature, said vasoocclusive coil having a proximal end and a distal end, said vasoocclusive coil being helically wound forming a lumen between said proximal and distal ends;

an inner reinforcement coil having a center, a proximal end and a distal end, said vasoocclusive coil being disposed about said inner reinforcement coil, said inner reinforcement coil being securely positioned within said vasoocclusive coil without being fixedly attached to said vasoocclusive coil;

an inner reinforcement stretch resistant member extending non-helically through the lumen of said vasoocclusive coil and externally of said inner reinforcement coil, said vasoocclusive coil and said inner reinforcement coil together forming a biplex coil, and said inner reinforcement stretch resistant member consisting of a non-metallic fiber material coated with a bioactive material, said inner reinforcement stretch resistant member having an end fixedly attached at or near the distal end of said vasoocclusive coil and said inner reinforcement coil of said biplex coil, said inner reinforcement stretch resistant member being configured to allow said vasoocclusive coil to be pushed after said vasoocclusive coil is partially deployed;

an inner strand of bioactive material disposed in the center of said inner reinforcement coil; and said inner reinforcement coil forming a helical winding wound in the same direction as said vasoocclusive coil winding.

20. The vasoocclusive device of claim 1, wherein said inner reinforcement stretch resistant member is radiopaque.

* * * * *